United States Patent [19]
Rosbash et al.

[11] Patent Number: 5,691,137
[45] Date of Patent: Nov. 25, 1997

[54] METHODS OF SCREENING CANDIDATE AGENTS FOR BIOLOGICAL ACTIVITY USING YEAST CELLS

[75] Inventors: Michael Rosbash, Newton Lower Falls; Francoise Stutz, Brookline, both of Mass.

[73] Assignee: Brandeis University, Waltham, Mass.

[21] Appl. No.: 297,808

[22] Filed: Aug. 30, 1994

[51] Int. Cl.$^6$ .............................. C12Q 1/11; C12N 15/00; C12N 7/04; C07H 21/04
[52] U.S. Cl. ...................... 435/6; 435/69.1; 435/172.1; 435/236; 530/388.21; 536/23.2; 536/24.1
[58] Field of Search ...................... 435/6, 172.3, 236, 435/172.1, 69.1; 530/300, 388.21; 536/23.2, 23.4, 24.1

[56] References Cited

U.S. PATENT DOCUMENTS

| | | | |
|---|---|---|---|
| 4,883,080 | 11/1989 | Brent et al. | 435/172.3 |
| 5,283,173 | 2/1994 | Fields et al. | 435/6 |

OTHER PUBLICATIONS

Lesser et al. Mutational analysis of pre-mRNA splicing in *Saccharomyces cerevisiae* using a sensitive new reporter gene, CUP1 Genetics vol. 133 851–863, 1993.

Cullen et al. The HIV–1 Rev protein: prototype of a novel class of eukaryotic post–transcriptional regulators Trends in Biol. Sci. vol. 16 346–350, 1991.

Bogerd et al. Genetic evidence that the Tat proteins of human immunodeficiency virus types 1 and 2 can multimerize in the eukaryotic cell nucleus J. Virol. vol. 67 5030–5034, 1993.

Zapp, M.L. and Green, M.R., "Sequence–Specific RNA Binding by the HIV–1 Rev Protein," *Nature*, 342:714–716 (1989).

Schena, M. and Yamamoto, K.R., "Mammalian Glucocorticoid Receptor Derivatives Enhance Transcription in Yeast," *Science*, 241: 965–967 (1988).

Séraphin, B and Rosbash, M., "Exon Mutations Uncouple 5' Splice Site Selection from U1 snRNA Pairing," *Cell*, 63:619–629 (1990).

Olsen, H.S. et al., "Secondary Structure is the Major Determinant for Interaction of HIV rev Protein with RNA," *Science*, 247:845–848 (1990).

Malim, M.H. et al., "Functional Dissection of the HIV–1 Rev Trans–Activator–Derivation of a Trans–Dominant Repressor of Rev Function," *Cell*, 58:205–214 (1989).

Emerman, M. et al., "The rev Gene Product of the Human Immunodeficiency Virus Affects Envelope–Specific RNA Localization," *Cell*, 57:1155–1165 (1989).

Daly, T.J. et al., "Specific Binding of HIV–1 Recombinant Rev Protein to the Rev–Responsive Element In Vitro," *Nature*, 342: 816–819 (1989).

Legrain, P. and Rosbash, M., "Some Cis–and Trans–Acting Mutants for Splicing Target Pre–mRNA to the Cytoplasm," *Cell*, 57:573–583 (1989).

Chang, D.D. and Sharp, P.A., "Messenger RNA Transport and HIV rev Regulation," *Science*, 249:614–615 (1990).

Heaphy, S. et al., "HIV–1 Regulator of Virion Expression (Rev) Protein Binds to an RNA Stem–Loop Structure Located Within the Rev Response Element Region," *Cell*, 60:685–693 (1990).

Malim, M.H. et al., "HIV–1 Structural Gene Expression Requires Binding of the Rev Trans–Activator to its RNA Target Sequence," *Cell*, 60:675–683 (1990).

Malim, M.H. et al., "The HIV–1 rev Trans–Activator Acts Through a Structured Target Sequence to Activate Nuclear Export of Unspliced Viral mRNA," *Nature*, 338:254–257 (1989).

Pikielny, C.W. and Rosbash, M., "mRNA Splicing Efficiency in Yeast and the Contribution of Nonconserved Sequences," *Cell*, 41:119–126 (1985).

Jacquier, A. et al., "A Quantitative Analysis of the Effects of 5" Junction and Tactaac Box Mutants and Mutant Combinations on Yeast mRNA Splicing," *Cell*, 43:423–430 (1985).

Teem, J.L. and Rosbash, M., "Expression of a β–galactosidase Gene Containing the Ribosomal Protein 51 Intron is Sensitive to the rna2 Mutation of Yeast," *Proc. Natl. Acad. Sci. USA*, 80:4403–4407 (1983).

Séraphin, B. et al., "A U1 snRNA:pre–mRNA Base Pairing Interaction is Required Early in Yeast Spliceosome Assembly but Does Not Uniquely Define the 5" Cleavage Site," *EMBO J.*, 7(8):2533–2538 (1988).

Rymond, B.C. and Rosbash, M., "Yeast Pre–mRNA Splicing," In The Molecular and Cellular Biology of the Yeast Saccharomyces: Gene Expression, E.W. Jones, J.R. Pringle and J.R. Broach, Eds. (Cold Spring Harbor, New York: Cold Spring Harbor Laboratory Press), pp. 143–192 (1992).

Jacquier, A. and Rosbash, M., "RNA Splicing and Intron Turnover are Greatly Diminished by a Mutant Yeast Branch Point," *Proc. Natl. Acad. Sci. USA*, 83:5835–5839 (1986).

Liao, X. et al., "Universally Conserved and Yeast–Specific U1 snRNA Sequences are Important but not Essential for U1 snRNP Function," *Genes & Dev.*, 4:1766–1774 (1990).

Rymond, B.C. et al., "A Novel Role for the 3" Region of Introns in Pre–mRNA Splicing of *Saccharomyces cerevisiae*," *Genes & Dev.*, 1:238–246 (1987).

Cullen, B.R. and Malim, M.H., "The HIV–1 Rev Protein: Prototype of a Novel Class of Eukaryotic Post–Transcriptional Regulators," *Trends Biol. Sci.*, 16:346–350 (1991).

Alani, E. et al., "A Method for Gene Disruption That Allows Repeated Use of URA3 Selection in the Construction of Multiply Disrupted Yeast Strains," *Genetics*, 116:541–545 (1987).

Bitter, G.A. and Egan K.M., "Expression of Heterologous Genes in *Saccharomyces cerevisiae* From Vectors Utilizing the Glyceraldehyde–3–Phosphate Dehydrogenase Gene Promoter," *Gene.*, 32:263–274 (1984).

(List continued on next page.)

*Primary Examiner*—James Ketter
*Assistant Examiner*—John S. Brusca
*Attorney, Agent, or Firm*—Hamilton, Brook, Smith & Reynolds, P.C.

[57] ABSTRACT

Methods of identifying and screening for agents with biological activity against target molecules using yeast cell cultures are described.

6 Claims, 7 Drawing Sheets

OTHER PUBLICATIONS

Hadzopoulou–Cladaras, M. et al., "The rev(trs/art) Protein of Human Immunodeficiency Virus Type 1 Affects Viral mRNA and Protein Expression via a cis–Acting Sequence in the env Region," *J. of Virology*, 63(3):1265–1274 (1989).

Fogel, S. and Welch J.W., "Tandem Gene Amplification Mediates Copper Resistance in Yeast," *Proc. Natl. Acad. Sci. USA*, 79:5342–5346 (1982).

Huang, X. et al., "Minimal Rev–Response Element for Type 1 Human Immunodeficiency Virus," *J. Virology*, 65(4):2131–2134 (1991).

Malim, M.H. et al., "Mutational Definition of the Human Immunodeficiency Virus Type Rev Activation Domain," *J. of Virology*, 65:4248–4254 (1991).

Feinberg, M.B. et al., "HTLV–III Expression and Production Involve Complex Regulation at the Levels of Splicing and Translation of Viral RNA," *Cell*, 46:807–817 (1986).

Kjems, J. et al., "Structural Analysis of the Interaction Between the Human Immunodeficiency Virus Rev Protein and the Rev Response Element," *Proc. Natal. Acad. Sci. USA*, 88:683–687 (1991).

Zapp, M.L. et al., "Oligomerization and RNA Binding Domains of the Type 1 Human Immunodeficiency Virus Rev Protein: A Dual Function for an Arginine–Rich Binding Motif," *Proc. Natl. Acad. Sci. USA*, 88:7734–7738 (1991).

Lesser, C.F. and Guthrie, C., "Mutational Analysis of Pre–mRNA Splicing in *Saccharomyces cerevisiae* Using a Sensitive New Reporter Gene, CUP1," *Genetics*, 133:851–863 (1993).

Parker, R. and Guthrie, C., "A Point Mutation in the Conserved Hexanucleotide at a Yeast 5" Splice Junction Uncouples Recognition, Cleavage, and Ligation," *Cell*, 41:107–118 (1985).

Wain–Hobson, S. et al., "Nucleotide Sequence of the AIDS Virus, LAV," *Cell*, 40:9–17 (1985).

Karin, M. et al., "Primary Structure and Transcription of an Amplified Genetic Locus: The CUP1 Locus of Yeast," *Proc. Natl. Acad. Sci. USA*, 81:337–341 (1984).

Sodroski, J. et al., "A Second Post–Transcriptional Trans–Activator Gene Required for HTLV–III Replication," *Nature*, 321:412–417 (1986).

Felber, B.K., et al., "Rev Protein of Human Immunodeficiency Virus Type 1 Affects the Stability and Transport of the Viral mRNA," *Proc. Natl. Acad. Sci. USA*, 86:1495–1499 (1989).

Hamer, D.H. et al., "Function of Autoregulation of Yeast Copperthionein," *Science*, 228:685–690 (1985).

Trono, D. and Baltimore, D., "A Human Cell Factor is Essential for HIV–1 Rev Action," *EMBO J.*, 9(12):4155–4160 (1990).

Malim, M.H. and Cullen, B.R., "Rev and the Fate of Pre–mRNA in the Nucleus: Implications for the Regulation of RNA Processing in Eukaryotes," *Mol. and Cell. Biol.*, 13(10):6180–6189 (1993).

Ito, H. et al., "Transformation of Intact Yeast Cells Treated with Alkali Cations," *J. Bacter.*, 153(1):163–168 (1983).

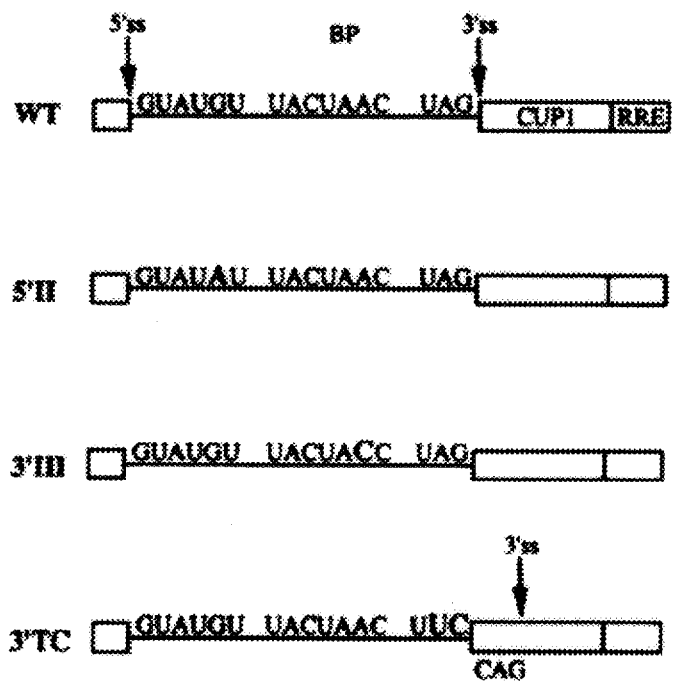
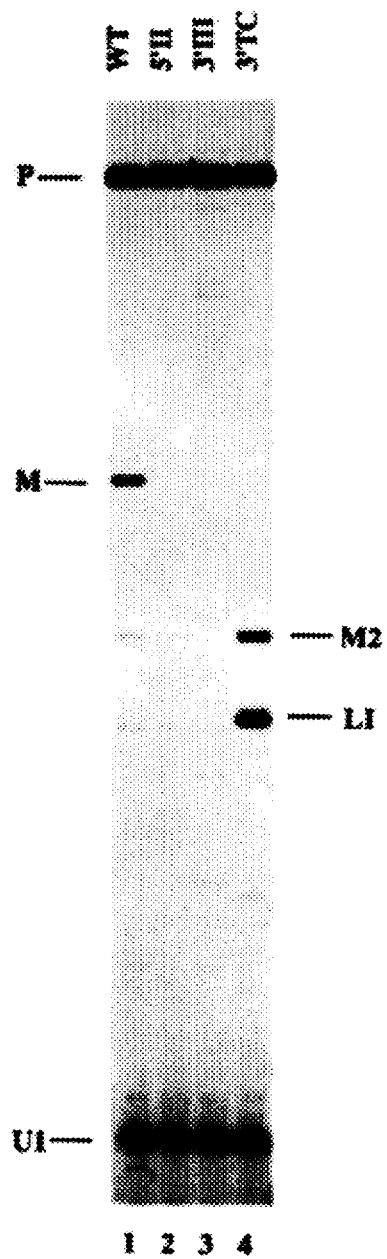
FIG.5A
FIG.5B

METHODS OF SCREENING CANDIDATE AGENTS FOR BIOLOGICAL ACTIVITY USING YEAST CELLS

GOVERNMENT SUPPORT

The invention described herein was supported, in whole or in part, by a grant from the National Institutes of Health. The United States Government has certain rights in this invention.

BACKGROUND OF THE INVENTION

A significant number of diseases afflicting mammals involve key molecules that control critical biological functions. For example, a particular protein may be required for the growth of a mammalian cell, or for a virus or bacteria that infects a mammalian cell.

Assay methods that rapidly and efficiently identify, or screen compounds for specific biological activity against these key target molecules are extremely valuable in the fields of medical and biological research. Such assay methods can be used to identify compounds useful in the treatment of a disease, or to further elucidate the molecular basis of the disease.

However, many assays currently in use are negative selection assays. A negative selection assay is an assay where the inhibition of a target molecule by a specific compound results in a negative effect, such as decreased expression of the target protein, which is subsequently detected by, for example, polyacrylamide gel electrophoresis (PAGE), or enzyme activity. Such assays are often relatively insensitive to compounds exhibiting minor effects. However, the identification of compounds with even minor effects can lead to major therapeutic advances in the treatment of a disease. Therefore, some compounds potentially useful as therapeutics remain undetected using these conventional screening assays. Moreover, these assays are also often time-consuming and tedious to perform, making it difficult to screen large numbers of compounds. Finally, compounds with toxic effects often score poorly in such assays, as the non-specific toxic effect can mask specific activity of the compound.

It is apparent that a need still exists for a rapid and efficient method with sufficient sensitivity to identify and screen compounds for biological activity against target molecules.

SUMMARY OF THE INVENTION

The present invention relates to methods of identifying and screening for agents with biological activity against target molecules. More specifically, the present invention relates to a positive selection assay using yeast cells as host cells to identify agents that inhibit the biological activity of a target molecule. The positive selection methods of the present invention permit the identification of agents with specific activity against a target molecule whose activity in yeast is indirectly measured with a growth assay. The positive selection assay of the present invention uses an appropriate yeast strain, defective in a designated biological activity; a recombinant reporter construct comprising a reporter gene encoding an activity which complements the defect in the yeast strain, the expression of the reporter gene being under the control of the target molecule; and a recombinant plasmid capable of expressing the target molecule.

In the positive selection methods of the present invention, identification of an agent with biological activity against a target molecule is determined by evaluating the effect of the agent on the growth of a yeast double transformant under restrictive culture conditions. A yeast double transformant is produced by introducing into a defective yeast host cell two recombinant constructs. The defective yeast strain is a yeast strain which is defective in a designated biological activity. The first recombinant construct is referred to herein as a reporter construct. The reporter construct contains a reporter gene which encodes an activity which complements the defect in the yeast host cell. The second recombinant construct is referred to herein as a recombinant expression plasmid. The expression plasmid contains a gene that encodes a target molecule. The target molecule has specific biological activity that controls the expression of the reporter gene in the yeast host cell. This yeast double transformant is cultured under permissive culture conditions. Under these conditions, the defective yeast strain will grow without the biological activity encoded for by the reporter construct.

The candidate agent to be tested for biological activity against the target molecule is then introduced into the cell culture medium, or into the yeast double transformant. The candidate agent is introduced in an amount which would produce a detectable positive growth response. After introducing the candidate agent, the culture conditions are altered, resulting in restrictive growth conditions that require expression of the reporter gene for growth of the yeast double transformant. For example, the yeast double transformant is subjected to a sufficiently high concentration, or sufficiently low concentration of a nutritive, or toxic, substance for sufficient time to kill or severely retard the growth of those yeast double transformants in which the activity of the target molecule is not inhibited. The growth rate of the yeast double transformant is then determined. If the activity of the target molecule is inhibited by the candidate agent, reporter gene expression is increased, conferring on the yeast double transformant the detectable advantage of growth, or more rapid growth, under restrictive conditions. The growth rate of the yeast double transformant in the presence of the candidate agent is compared with the growth rate of the yeast double transformant grown under similar conditions but without the presence of the candidate agent to determine if the candidate agent has biological activity against the target molecule.

The present invention further relates to agents that inhibit the biological activity of the target molecule which are identified using the positive selection methods described herein. Agents that inhibit the biological activity of the target molecule increase the growth rate of yeast double transformants relative to the growth of yeast double transformants in which the activity of the target molecule is not inhibited. Such agents are useful in the treatment of diseases caused by, or aggravated, by the activity of the target molecule.

The present invention further relates to yeast strains engineered to be defective in a biological activity required for growth under defined conditions and to recombinant reporter gene constructs which complement the defect and which are suitable for use in the above-described methods. Reporter gene constructs suitable for use in the methods of the present invention comprise a sequence encoding a reporter gene operably linked to regulatory sequences comprising transcriptional and translational elements which are compatible to the yeast host cell, and thus, are sufficient for the reporter gene to be expressed in the yeast host cell.

Also encompassed by the present invention are recombinant expression plasmids suitable for use in the above-described methods. Such expression plasmids contain nucleic acid sequence inserts which encode a target molecule operably linked to regulatory sequences which are compatible with yeast host cells.

Thus, as described herein, the present invention provides a positive selection assay to rapidly identify and screen for target molecules with activity in eukaryotic cells. The methods of the present invention are extremely sensitive. For example, using the methods described herein, compounds with even minor effects can be identified by positive selection and further refined for use as effective therapeutic agents. Such compounds often go undetected in conventional negative selection methods. In particular, the use of yeast cells or host cells makes the methods described herein easy to perform and amenable to large scale screening procedures.

BRIEF DESCRIPTION OF THE DRAWINGS

FIG. 5A is a schematic drawing of the pre-mRNAs encoded by wild-type or mutant PC-CUP-RRE constructs.

FIG. 5B is an autoradiograph showing the results of experiments determining CUP1 pre-mRNA and mRNA levels in yeast strains containing wild-type or mutant PC-CUP-RRE constructs.

DETAILED DESCRIPTION OF THE INVENTION

Figure 1:
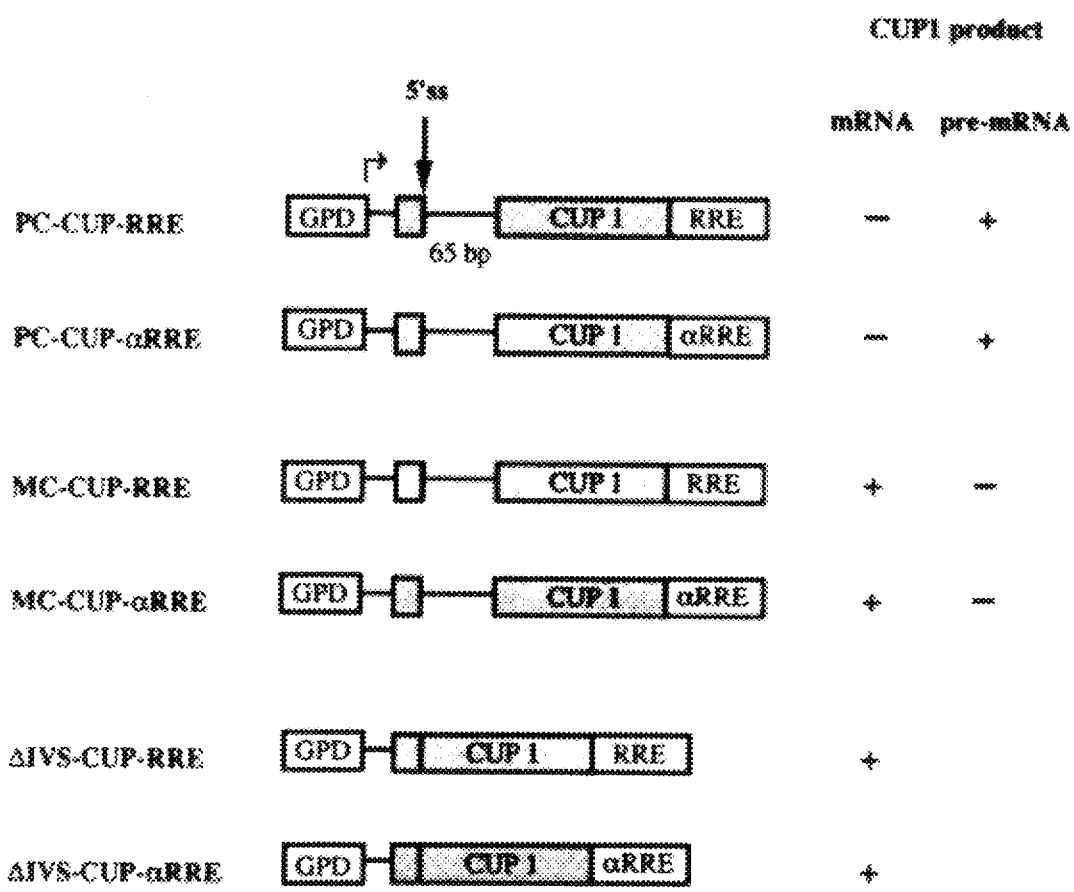
FIG. 1 is a schematic representation showing the CUP1 reporter constructs.

The present invention relates to methods of identifying and screening for agents with biological activity against target molecules. Candidate agents can be tested by the methods of this invention to determine their activity against target molecules. The terms "candidate agent" or "drug" as used herein encompass small molecules (e.g., small organic molecules), peptides, antibodies or antibody fragments, or nucleic acid sequences, including DNA and RNA sequences. The term "target molecule" as used herein, encompasses peptides, proteins and nucleic acid sequences, both DNA or RNA, produced by, or present in mammalian cells, bacteria or viruses. Target molecules suitable for use in the present invention typically possess a biological activity, or function, which is critical for the growth, proliferation or differentiation of a eukaryotic cell, or of a bacteria or virus capable of entering and infecting a eukaryotic cell. Such target molecules include, for example, proteins necessary for viral replication or viral gene expression, eukaryotic transcription factors, enzymes such as protein kinases, and cytokines involved in cellular differentiation.

More specifically, the present invention relates to a positive selection assay using yeast cells as host cells to identify candidate agents that inhibit the biological activity of a target molecule. In a preferred embodiment of the present invention S. cerevisiae yeast cells are used as the host cells. Yeast cells were selected for use in the present method because transcription and translation processes in yeast are similar, if not identical, to processes that occur in mammalian cells. However, yeast cells are often more amenable to genetic manipulation than mammalian cells, and they grow much more rapidly. Thus, yeast cells provide an excellent model for the study of eukaryotic gene expression.

The positive selection assay of the present invention uses an appropriate yeast strain, defective in some activity; a recombinant reporter construct comprising a reporter gene encoding an activity which complements the defect in the yeast strain, the expression of said gene being under the control of the target molecule; and a recombinant plasmid capable of expressing the target molecule in yeast. The positive selection assay methods of the present invention permits the identification of agents with specific activity against a target molecule whose activity in yeast is indirectly measured with a growth assay.

A defective yeast strain is a yeast strain defective in a designated biological activity. Preferably this biological activity is related to the growth of the yeast strain in a manner that allows detection of that activity with a growth assay. For example, a specific growth activity can be the expression of a growth factor, such as a protein, or enzyme which, although not required for the growth of the yeast strain under one set of defined conditions (referred to herein as permissive conditions) is required for the growth of the yeast strain under another set of defined conditions (referred to herein as restrictive conditions). Thus, a defective yeast stain is designed which is defective in a specific growth activity resulting in a yeast strain capable of growth under permissive conditions, but which lacks an essential factor which permits the growth of the yeast strain under restrictive conditions. This defective yeast strain will grow under permissive culture conditions, but when the culture conditions are altered to restrictive conditions, the yeast strain is incapable of growing unless the specific growth activity is exogenously supplied, or provided to the strain by the addition of a gene or genes through recombinant DNA technology. The defective yeast strain can be constructed using standard genetic engineering techniques known to those of skill in the art.

Alternatively, a defective yeast strain suitable for use in the present invention can be a yeast strain that has a naturally-occurring defect, or a defect induced by culture conditions. For example, a yeast strain may be obtained that, in its natural state, lacks a particular enzyme or protein which would permit the yeast cells to grow under specific conditions. In this case, no genetic manipulation would be necessary to obtain a defective yeast strain. In either case, the defective yeast strain is defective in a designated biological activity. Typically, the defective yeast strain is constructed by deletion mutation of one, or more gene sequence, or sequences, encoding the specific growth activity. The construction of a yeast strain lacking a copper chelator protein, CUP1, is described in detail in Example 1.

A reporter gene construct is then designed to encode a growth activity which complements the defect of the yeast strain. The growth activity is encoded by one, or more, nucleic acid sequence, or sequences, inserted into the construct. The reporter gene construct also contains regulatory sequences necessary to allow the expression of the reporter gene construct in eukaryotic cells, such as yeast. The growth activity encoded by the reporter gene construct supplies a growth activity which is identical to, or substantially similar to, the activity deleted from the defective yeast construct and is sufficient to permit the growth of the defective yeast strain under restrictive conditions. Thus, if the reporter construct is introduced into the defective yeast strain and the reporter gene encoding the activity is expressed, the defective yeast strain will grow under restrictive conditions. The expression of, or the activity of, the growth factor encoded by the reporter gene is detected by a growth assay that determines the positive growth rate of the defective yeast strain under restrictive conditions.

A key feature of the positive selection assay method of the present invention is that the expression of the reporter gene is designed to be under the control of the target molecule. More specifically, the target molecule possesses a biological activity that inhibits the expression of, or the biological activity of, the reporter gene construct. The activity of the target molecule can be directed toward the encoded growth activity itself, or toward the regulatory sequences that allow the expression of the growth activity. In either case, the growth rate of the defective yeast strain under restrictive conditions is a function of the biological activity of the target molecule. If the target molecule is introduced into the defective yeast strain and the target molecule has biological activity, the expression of the reporter gene is inhibited and the defective yeast strain will not grow, or only grow poorly, under restrictive conditions. However, if the biological activity of the target molecule is reduced, or completely inhibited, the reporter gene is expressed, and the defective yeast strain will grow (or grow more rapidly relative to a defective yeast strain in which the target molecule has biological activity) under restrictive conditions. Thus, an agent, such as a drug that inhibits the activity of the target molecule, will alter the growth rate of the defective yeast strain in a detectable manner. The reporter gene construct can be made using standard genetic engineering techniques known to those of skill in the art. The construction of a reporter gene construct encoding a copper chelator protein, CUP1, is described in detail in Example 1. This reporter gene construct is designed such that the mRNA encoding the CUP1 protein must be properly spliced for translation and expression of the CUP1 protein in yeast.

An expression plasmid is also constructed which encodes the target molecule, and includes the regulatory sequences necessary to allow expression of the plasmid in yeast. The construction of such an expression plasmid uses standard genetic engineering techniques known to those of skill in the art. The construction of an expression plasmid which encodes the target molecule, HIV-1 Rev protein, is described in detail in Example 1.

In one embodiment of the present invention, a reporter gene construct and an expression plasmid containing a gene encoding the target molecule are introduced into the defective yeast strain, thereby producing a yeast double transformant. Introduction of the reporter gene construct and expression plasmid into yeast cells can be accomplished by standard laboratory techniques for example, such as transfection by calcium phosphate precipitation, or electroporation. Introduction of the reporter gene construct and expression plasmid into the yeast host cell can be substantially simultaneously, or sequentially. Introduction of the reporter gene construct and expression plasmid into the defective yeast strain results in a yeast double transformant.

The yeast double transformant is cultured under permissive growth conditions for a time sufficient to allow the yeast double transformants to recover and to establish proliferating yeast cells, typically three to five days. The yeast double transformant is then contacted with a candidate agent to be tested for activity against the target molecule. Typically, the candidate agent is solubilized in culture media, or a buffer and added directly to the culture medium surrounding the yeast double transformant. A single concentration of candidate agent can be tested, or a range of concentrations can be tested using several cultures of yeast double transformant. If the candidate agent is a nucleic acid, such as, for example, an anti-sense nucleic acid sequence, the candidate agent can be introduced into the yeast double transformant by transfection or electroporation or other methods known to those of skill in the art.

The culture conditions of the yeast double transformant are then altered, resulting in restrictive growth conditions that require expression of the reporter gene for growth of the yeast double transformant. Alteration of culture conditions can include, for example, a change in the concentration of a component of the culture medium either increasing, or decreasing the concentration, or adding or deleting a medium component altogether. Additionally, alteration of culture conditions can also include a change in temperature or a change in atmosphere. The alteration of the culture conditions can be in a single step where cells are placed in a petri dish under the restrictive conditions, or can be stepwise, e.g., over a series of steps such as gradually increasing the concentration of a culture medium ingredient. The yeast double transformant is maintained under the restrictive culture conditions for a time sufficient for a detectable change in growth rate to occur.

The growth rate of the yeast double transformant under restrictive conditions, is then determined. This is typically accomplished by a growth assay which measures the growth rate of the yeast double transformant. If the candidate agent does not have activity against the target molecule, the target molecule exerts its control over the expression of the reporter gene, the reporter gene is not expressed, and the growth rate of the yeast double transformant is substantially decreased, or completely inhibited. If the candidate agent has activity against the target molecule, the target molecule's control over the expression of the reporter gene is inhibited, the reporter gene is expressed and the yeast double transformant grows, or the growth rate is increased under the restrictive conditions. Thus, the method of the present invention presents a positive selection method for effective candidate agents.

Agents that enhance growth non-specifically (i.e., artificially) are identified much less frequently than those agents that inhibit growth non-specifically, for example, due to toxic effects. However, even this potential source of noise can be screened out by the use of a genetically marked yeast control strain. The yeast control strain contains a reporter, or selectable marker which permits the growth rate of the control strain to be determined. For example, the control yeast strain can encode the enzyme, $\beta$-galactosidase. The expression of this enzyme can be measured using a conventional colorimetric assay or by counting colored colonies on appropriate indicator plates, as described in Legrain, P. and Rosbash, M., "Some cis- and trans-acting mutants for splicing target pre-mRNA to the cytoplasm," Cell, 57:573–583 (1989). The candidate agent is contacted with both the yeast double transformant strain and the yeast control strain and the ratio of the growth rate of the yeast double transformant and the yeast control strain is determined. A candidate agent that has specific activity against the target molecule will enhance the growth ratio of the yeast double transformant cells to the cells of the control strain. Non-specific effects will impact both strains essentially identically and will not change the ratio of the growth rate of the yeast double transformant strain to the control strain.

The strategy of the positive selection yeast assay is especially amenable to small scale approaches to drug screening. Large numbers of candidate drugs, or groups of drugs, can be assayed rapidly. Once a candidate drug is identified, it can be further tested for activity in mammalian systems. Once activity is confirmed, modified drugs could then be synthesized and assayed in other conventional drug testing protocols.

In another embodiment of the present invention, a library of nucleotide or amino acid sequences can be rapidly screened to determine the biological activity of their encoded peptides against a target molecule. If the activity of the target molecule inhibits growth, e.g., as in the Rev function assay described below, it is reasonable to select in vivo for nucleic acid sequences, or amino acid sequences that encode peptides or proteins that inhibit the activity of the target molecule. The strategy is straightforward and represents an "in vivo selex" approach. A library of random peptide or nucleotide sequences can be expressed in the yeast double transformant strain and one can identify those encoded sequences that inhibit the target molecule activity, for example, by growth enhancement. For example, plasmids containing DNA sequence inserts obtained from a library of DNA sequences can be introduced into the yeast double transformants of the present invention. The generation of DNA libraries and the insertion of random DNA sequences into expression plasmids are techniques well known to those of skill in the art. The expression plasmids contain regulatory sequences required for the expression of the DNA sequences in yeast cells. Introduction of these plasmids into the yeast double transformants can be accomplished, for example, by transfection using standard laboratory techniques. After transfection with the plasmids, the yeast double transformants are maintained for a time sufficient to recover from the transfection process and to express the encoded DNA sequences. The culture conditions are then altered to restrictive conditions and the transformants are maintained under these conditions for a time sufficient to kill, or severely retard the growth of transformants in which the activity of the target molecule is not inhibited. If the expressed DNA sequence within a particular transformant inhibits the target molecule, the transformant will grow, or grow more rapidly relative to the transformants in which the activity of the target molecule is not inhibited. Only a tiny growth advantage is required for a particular transformant to overtake a population within a few days. The growing transformants can be harvested from culture and the DNA contained within these recovered and sequenced using known laboratory techniques. Thus, DNA sequences that possess positive activity can be readily identified. The best set of inhibitor sequences will self-select as the most rapidly growing strains. The effect of these specific molecules on the activity of the target molecule can then be assayed directly, both in yeast and mammalian cells. Further rounds of iterative selection can then be designed to identify better inhibitors, or one can attempt to treat cells with drugs with a similar molecular design.

The positive selection yeast assay can be used to identify candidate agents against the HIV-1 Rev protein. The HIV-1 Rev protein, a 116 amino acid protein, is a crucial regulator of the HIV-1 virus life cycle (Feinberg, M. B., et al., "HTLV-III expression and production involve complex regulation at the levels of splicing and translation of viral RNA," Cell, 46:807–817 (1986); Sodroski, J., et al., "A second post-transcriptional trans-activator gene required for HTLV-III replication," Nature, 321:412–417 (1986)). In its absence, viral transcripts that are unspliced or partially spliced accumulate in the nucleus. Rev expression results in the appearance of these transcripts in the cytoplasm where they encode the viral structural proteins Env, Gag and Pol. In certain experimental systems, including COS cells but not T lymphocytes, this relocalization is accompanied by a reduction in the cytoplasmic levels of fully spliced mRNAs, including Rev mRNA itself (Malim, M. H., et al., "Functional dissection of the HIV-1 Rev trans-activator—derivation of a trans-dominant repressor of Rev function," Cell 58:205–214 (1989)); Emerman, M., et al., "The rev gene product of the human immunodeficiency virus affects envelope-specific RNA localization," Cell, 57:1155–1165 (1989); Felber, B. K., et al., "Rev protein of human immunodeficiency virus type 1 affects the stability and transport of the viral mRNA," Proc. Natl. Acad. Sci. USA, 86:1495–1499 (1989); Malim, M. H. and Cullen, B. R., "Rev and the fate of pre-mRNA in the nucleus: implications for the regulation of RNA processing in eukaryotes," Mol. Cell. Biol., 13(10):6180–6189 (1993)). The export activity is mediated in part by the interaction of Rev with the Rev response element (RRE), a highly structured 240 base RNA sequence located in the viral Env gene (Hadzopoulou-Cladaras, et al., "The rev 28 (trs/art) protein of human immunodeficiency virus type 1 affects viral mRNA and protein expression via a cis-acting sequence in the env region," J. Virol., 63:1265–1274 (1989); Daly, T. J., et al., "Specific binding of HIV-1 recombinant Rev protein to the Rev-responsive element in vitro," Nature, 342:816–819 (1989); Zapp, M. L. and Green, M. R., "Sequence-specific RNA binding by the HIV-1 Rev protein," Nature, 342:714–716 (1989); Heaphy, S., et al., "HIV-1 regulator of virion expression (Rev) protein binds to an RNA stem-loop structure located within the Rev response element region," Cell, 60:685–693 (1990); Malim, M. H., et al., "HIV-1 structural gene expression requires binding of the Rev trans-activator to its RNA target sequence," Cell, 60:675–683 (1990); Olsen, H. S., et al., "Secondary structure is the major determinant for interaction of HIV rev protein with RNA," Science, 247:845–848 (1990); Huang, X., et al., "Minimal Rev-response element for type 1 human immunodeficiency virus," J. Virol., 6(4):2131–2134 (1991); Kjems, et al., "Structural analysis of the interaction between the human immunodeficiency virus Rev protein and the Rev response element," Proc. Natl. Acad. Sci. USA, 88:683–687 (1991)).

A positive selection yeast assay was designed to identify and screen candidate agents for activity against the HIV-1 Rev protein. An expression plasmid encoding HIV-1 Rev was constructed as described in Example 1. The RNA sequence with which Rev interacts (called the Rev Response Element, or RRE) was inserted into a reporter gene construct, also as described in Example 1. The reporter gene construct also contained a synthetic intron comprising a nucleic acid sequence approximately 65 base pairs in length, as described in Legrain, P. and Rosbash, M., "Some cis- and trans-acting mutants for splicing target pre-mRNA to the cytoplasm," Cell, 57:573–583 (1989). As described in Example 1, the synthetic intron interrupts the reporter gene coding sequence and contains a consensus 5' splice site, branchpoint and 3' splice site sequences. By placing the RRE sequence in the reporter gene construct, the activity encoded by the reporter gene was sensitive to Rev function. Because the reporter gene contained an intron, the presence of Rev inhibits splicing and promoted pre-mRNA transport to the cytoplasm. A defective yeast strain was designed as described in Example 2. The defective yeast strain lacked a coding sequence for a copper chelator protein, CUP1, which is required for the yeast strain to grow in copper-containing medium.

The yeast reporter gene, CUP1, was chosen because it confers resistance to copper in a dose-dependent manner. (Hamer, D. H., Thiele, D. J., and Lemontt, J. E., "Function and autoregulation of yeast copperthionein," *Science*, 228:685–690 (1985); Lesser, C. F. and Guthrie, C., "Mutational analysis of pre-mRNA splicing in *Saccharomyces cerevisiae* using a sensitive new reporter gene, CUP1," *Genetics*, 133(4):851–863 (1993)), and thus, it encodes an activity that can be scored by growth. The presence of biologically active Rev protein will inhibit the growth of a yeast strain containing a reporter gene construct that carries the RRE sequence on a pre-mRNA from which only the mRNA product is translatable. That is, the nucleic acid sequence encoding CUP1 was inserted into the reporter gene construct in such a manner that the CUP1 product is translated only from correctly spliced mRNA. This was accomplished by encoding the synthetic intron sequence out-of-frame (i.e., in a different reading frame) with the sequence encoding the CUP1 protein, thus, only permitting the expression of CUP1 protein from mRNA (spliced RNA) but not from pre-mRNA (unspliced RNA). In this case, copper resistance reflects mRNA levels and is a function of splicing efficiency. If Rev is present, Rev will bind to the RRE of the reporter construct and an increased amount of pre-mRNA will be exported to the cytoplasm. The pre-mRNA is not translated into CUP1 product. If the activity of Rev is inhibited, Rev will not bind to RRE and a maximum amount of RNA encoding the CUP1 is spliced and maximum levels of mRNA are translated to CUP1 product. The expression of the CUP1 protein permits the defective yeast strain to grow on culture medium containing copper.

If a candidate agent (i.e., an agent to be tested for activity against the Rev protein) is introduced into the culture medium in which the yeast double transformant is growing, the activity of that candidate agent against the Rev protein can be evaluated by measuring the growth rate of the yeast double transformant under restrictive conditions (i.e., increasing copper concentration).

The results reported herein in Examples 2-4 indicate that important aspects of Rev function can be recapitulated in *S. cerevisiae*. In yeast, as in a number of mammalian systems, Rev promotes the export of pre-mRNA, which is accompanied by a negative effect on splicing. Biological activity is dependent on intact Rev effector and RNA binding/oligomerization domains as well as on an RRE in the target pre-mRNA transcript. In earlier experiments similar intron-containing transcripts encoding β-galactosidase rather than CUP1 were assayed. When Rev was expressed from a high copy number plasmid, an RRE-independent increase in pre-mRNA export and decrease in pre-mRNA splicing were detectable.

Although the direct cellular targets of Rev have not been identified, it has been proposed that they are components of the splicing or spliceosome assembly machinery (Chang, D. D. and Sharp, P. A., "Messenger RNA transport and HIV rev regulation," *Science*, 249:614–615 (1990); Cullen, B. R. and Malim, M. H., "The HIV-1 rev protein: prototype of a novel class of eukaryotic post-transcriptional regulators," *Trends Biol. Sci.*, 16:346–350 (1991)). A competing hypothesis is that Rev's primary function is to promote transport directly (Felber, B. K., et al., "Rev protein of human immunodeficiency virus type 1 affects the stability and transport of the viral mRNA," *Proc. Natl. Acad. Sci. USA*, 86:1495–1499 (1989); Malim, M. H. and Cullen, B. R., "Rev and the fate of pre-mRNA in the nucleus: implications for the regulation of RNA processing in eukaryotes," *Mol. Cell. Biol.*, 13(10):6180–6189 (1993)). Without splice sites or with very efficient splicing signals, nuclear pre-mRNA may adopt other fates that mask or are otherwise incompatible with Rev regulation, e.g., nuclear degradation efficient transport to the cytoplasm, or efficient splicing. In this view, inefficient splice sites may be required to accumulate high levels of nuclear pre-mRNA which can then interact with Rev.

Indeed, the small synthetic intron present in the CUP1 reporter constructs is inefficiently spliced and leads to the accumulation of high pre-mRNA levels. Yet only a small fraction of pre-mRNA escapes from the nucleus and is translated in the cytoplasm. These observations are entirely consistent with earlier analyses of this intron in the context of a β-galactosidase reporter gene construct. Based on this translation criterion, most of the pre-mRNA was retained within the nucleus, at least in part through an interaction with splicing factors (Legrain, P. and Rosbash, M., "Some cis- and trans-acting mutants for splicing target pre-mRNA to the cytoplasm," *Cell*, 57:573–583 (1989)). These arguments indicate that most of the CUP1 pre-mRNA is recognized by early splicing factors and is "committed" to the splicing pathway. In this system, pre-mRNA translation therefore reflects pre-mRNA transport and is inversely proportional to pre-mRNA retention or commitment.

Thus, as a result of the work presented herein, agents can be identified that are useful in the treatment of HIV-1 infection, as well as HIV-2 infections, in eukaryotic cells. More specifically, an effective amount of an agent identified by the present invention can be used to treat an individual infected with HIV-1. An effective amount of an identified agent is an amount of agent sufficient to inhibit the activity of HIV-1 Rev protein, specifically, for example, the binding of HIV-1 Rev protein to the Rev Response Element.

Administration of such identified agents can be by medically accepted techniques, including intravenous, subcutaneous, or oral administration. Appropriate amounts, or effective doses, will, of course, vary from individual to individual and by type of infection and severity of infection. Appropriate dosages can be calculated by those of skill in the art taking such factors into account.

The present invention will now be illustrated by the following examples, which will further and more specifically illustrate the invention.

Example 1: Reporter Constructs and Plasmid Constructs

Reporter Constructs

The CUP1 reporter constructs were obtained by cloning two PCR amplified fragments (the intron and the CUP1 coding region) into the BamHI site of the pG1 (Bitter, G. A. and Egan, K. M., "Expression of heterologous genes in *Saccharomyces cerevisiae* from vectors utilizing the glyceraldehyde-3-phosphate dehydrogenase gene promoter," *Gene*, 32:263–274.(1984); Schena, M. and Yamamoto, K. R., "Mammalian glucocorticoid receptor derivatives enhance transcription in yeast," *Science*, 241:965–967 (1988)) TRP/2 μm expression vector in a three way ligation. The intron fragment was obtained by PCR amplification of the pLGNdeAcc or pLGAcc constructs (Legrain, P. and Rosbash, M., "Some cis- and trans-acting mutants for splicing target pre-mRNA to the cytoplasm," *Cell*, 57:573–583 (1989)). The primers used to amplify pLGNdeAcc (DT2967 and DT2889) and pLGAcc (DT2967 and DT9888) introns introduced an BamHI site at the 5' end and a SmaI site at the 3' end of the fragments. In addition, the 5' primer DT2967 introduced a sequence of 11 nucleotides downstream of the BamHI site corresponding to the yeast rp51A leader sequence (Teem, J. L. and Rosbash, M., "Expression of a β-galactosidase gene containing the ribosomal protein 51 intron is sensitive to the rna2 mutation of yeast," *Proc. Natl. Acad. Sci. USA*, 80:4403–4407 (1983)) and which improves the translation of the transcripts. The CUP1 gene coding fragment was obtained by PCR amplification of the CUP1 gene (Fogel, S. and Welch, J. W., "Tandem gene amplification mediates copper resistance in yeast," *Proc. Natl. Acad. Sci. USA*, 79:5342–5346 (1982); Karin, M., et al., "Primary structure and transcription of an amplified genetic locus: the CUP1 locus of yeast," *Proc. Natl. Acad. Sci. USA*, 81:337–341 (1984)) with primers DT2627 and DT2538 introducing a SmaI and BclI site respectively. The NdeAcc or Acc BamHI/SmaI intron fragments and the CUP1 SmaI/BclI fragment were ligated into the BamHI cut pG1 vector in a three way ligation to generate pG1PC-CUP and pG1MC-CUP respectively. In these constructs the SmaI site replaces the original ATG codon of the CUP1 coding sequence by a GGG codon. The initiation codon lies 11 bases downstream of the BamHI site and leads to the formation of a fusion protein containing 6 amino acids in front of the CUP1 sequence in the case of the pG1MC-CUP construct and 28 in the case of the pG1PC-CUP construct. The pG1ΔIVS-CUP construct was obtained by synthesizing two complementary oligos (DT2968 and DT2969) corresponding to an intronless version of pG1MC-CUP between the BamHI and SmaI sites. The oligos were annealed, cut with BamHI and SmaI and cloned into pG1MC-CUP to replace the already existing BamHI-SmaI insert.

A 450 fragment containing the whole RRE was obtained by PCR amplification between positions 7660 and 8110 of the HIV env gene (Wain-Hobson, et al., "Nucleotide sequence of the AIDS virus, LAV," *Cell*, 40:9–17 (1985)) using two primers (DT2162 and DT2163) which introduce a SalI site at the 5' end and a XhoI site at the 3' end of the fragment. This SalI-XhoI RRE fragment was cloned in either orientation into the SalI site of pG1PC-CUP, pG1Mc-CUP and pG1ΔIVS-CUP to generate the -RRE or a -αRRE versions of these constructs. The -RRE or α-RRE sequences are located after the CUP1 stop codon and upstream of the PGK terminator. The whole CUP1 transcription units were excised from the pG1 vector with HindIII and XbaI and recloned into the BamHI site of the LEU/2 μm vector (pJH21) using BglII linkers to generate the PC-CUP-RRE (αRRE), MC-CUP-REE(αRRE) and ΔIVS-cCUP-RRE (αRRE) constructs used for yeast transformation. The PC-5II-CUP-RRE, PC-3'III-CUP-RRE and PC-3'TC-CUP-RRE constructs were obtained by replacing the BamHI-SmaI of the wild-type PC-CUP-RRE construct by equivalent PCR fragments using mutated primers (DT3131 and DT2889, DT2967 and DT3200, DT2967 and DT3199, respectively) that contained the 5'II, 3'III or 3'TC mutations.

The six CUP1 gene reporter constructs used to examine Rev activity in yeast are described in FIG. 1. Each CUP1 transcription unit is driven by the strong glyceraldehyde-3-phosphate dehydrogenase (GPD) constitutive promoter (open box) (Bitter and Egan, 1984); the transcription initiation site is indicated by an arrow. The CUP1 coding region is shown as a shaded box. In the PC-CUP- and MC-CUP-constructs, a synthetic intron interrupts the CUP1 coding sequence after the third codon. The intron contains consensus 5' splice site, branchpoint and 3' splice site sequences. In the MC construct, the synthetic intron comprises 65 b.p. (GUAUGUUAAUAUGGUUAACGUCGCGACCGUGUU UUUGAUA UCUAUACUAACAGGCCUUUUAAUAG) SEQ ID NO: 1. In the PC construct, the synthetic intron comprises 65 b.p. (GUAUGUUAAUAUGGUUAACGUCGCGACCGUGUU UUUGAUAUCUAUACUAACAGGCCUU UUAAUAG) SEQ ID NO: 2. In the PC-CUP- constructs, CUP1 is encoded from the pre-mRNA only; in the MC-CUP-constructs, CUP1 is encoded from the spliced RNA only. The CUP1 coding ΔIVS- constructs contain no intron. For each type of construct, the complete RRE sequence was cloned right after the CUP1 stop codon in either the sense or anti-sense (RRE or α-RRE) orientation. All transcripts terminate beyond the RRE sequence within the phosphoglycerate kinase (PGK) terminator (not shown) (Schena, M. and Yamamoto, K. R., "Mammalian glucocorticoid receptor derivatives enhance transcription in yeast," *Science*, 241:965–967 (1988)).

Each type of reporter construct carries at its 3' end, after the CUP1 gene stop codon, a 450 bp fragment encoding the complete Rev response element in either the sense (-RRE) or anti-sense (α-RRE) orientation. The ΔIVS-CUP constructs were used as non-intron containing controls. The PC-CUP and MC-CUP constructs contain a 65 bp synthetic intron at the 5' end of the CUP1 coding sequence. In the PC-CUP (pre-mRNA coding-CUP) constructs, the intron sequence is in frame with the CUP1 coding sequence; the spliced mRNA is in another frame containing early stop codons, thus preventing CUP1 expression from the mRNA. For this type of construct, the ability to grow in the presence of copper is the result of pre-mRNA translation and is taken as a measure of pre-mRNA export. In contrast, the MC-CUP (mRNA coding-CUP) constructs encode the CUP1 product only from the spliced mRNA, whereas the pre-mRNA is out of frame. In this case, copper resistance reflects mRNA levels and is a function of splicing efficiency.

Expression Plasmid Construction

The Rev expressing plasmids were obtained by polymerase chain reaction amplification of wild-type or described mutant Rev sequences (Wain-Hobson, et al., "Nucleotide sequence of the AIDS virus, LAV," *Cell*, 40:9–17 (1985); Malim, M. H., et al., "The HIV-1 rev trans-activator acts through a structured target sequence to activate nuclear export of unspliced viral mRNA," *Nature*, 338:254–257 (1989)) with two oligo primers (DT2224 and DT2225) containing BclI sites. The 350 bp BclI Rev fragments were cloned into the BamHI sites of a centromeric derivative of the yeast TRP/2 μm expression vector pG1 (Bitter, G. A. and Egan, K. M., "Expression of heterologous genes in Saccharomyces cerevisiae from vectors utilizing the glyceraldehyde-3-phosphate dehydrogenase gene promoter," *Gene*, 32:263–274 (1984); Schena, M. and Yamamoto, K. R., "Mammalian glucocorticoid receptor derivatives enhance transcription in yeast," *Science*, 241:965–967 (1988)). A centromeric version of the pG1 plasmid was obtained by replacing the 2 kb EcoRI fragment containing the 2 μm sequence by the 2 kb BamHI fragment containing the CEN3 sequence and the 1.2 kb EcoRI fragment containing the ARS sequence of pXL8 (Liao, X., et al., "Universally conserved and yeast-specific U1 snRNA sequences are important but not essential for U1 snRNP function," *Genes Dev.*, 1766–1774 (1990)) using EcoRI linkers in a three way ligation. The Rev coding sequences are under the control of the strong constitutive glyceraldehyde 3-phosphate dehydrogenase (GPD) promoter and followed by the phosphoglycerate kinase (PGK) gene terminator.

Example 2: Yeast Strains and Copper Growth Assay

All the DNA constructs were transformed into the copper sensitive strain Y59ΔCUP1 (mat a, leu2-3, leu2-112, ura3-52, trpl-289, arg4, ade2, ΔCUP1). The copper sensitive strain was obtained by deleting the endogenous tandemly repeated X-CUP1 transcription units (Fogel, S. and Welch, J. W., "Tandem gene amplification mediates copper resistance in yeast," *Proc. Natl. Acad. Sci. USA*, 79:5342-5346 (1982); Karin, M., et al., "Primary structure and transcription of an amplified genetic locus: the CUP1 locus of yeast," *Proc. Natl. Acad. Sci. USA*, 81:337-341 (1984); Hamer, D. H., Thiele, D. J., and Lemontt, J. E., "Function and autoregulation of yeast copperthionein," *Science*, 228:685-690 (1985)) of the MGD353-13D strain (Séraphin, B., Kretzner, L., and Rosbash, M., "A U1 snRNA: pre-mRNA base pairing interaction is required early in yeast spliceosome assembly but does not uniquely define the 5' cleavage site," *EMBO J.*, 7:2533-2538 (1988)) by homologous recombination using a construct that contained the HisG-URA-HisG 3.8Kb fragment (Alani, E., et al., "A method for gene disruption that allows repeated use of URA3 selection in the construction of multiply disrupted yeast strains," *Genetics*, 116:541-545 (1987)) flanked by 0.8 or 1.7 kb of DNA derived from the 5' or 3' unique genomic DNA regions adjacent to the repeated X-CUP1 locus. Homologous recombinants were tested by absence of growth on 0.1 mM copper; uracil auxotrophy of copper sensitive strains was recovered by growth on FOA (Alani, E., et al., "A method for gene disruption that allows repeated use of URA3 selection in the construction of multiply disrupted yeast strains," *Genetics*, 116:541-545 (1987)). The CUP1 reporter constructs were cotransformed with the Rev expressing plasmids into the Y59ΔCUP1 strain according to standard procedures (Ito, H., et al., "Transformation of intact yeast cells treated with alkali cations," *J. Bacteriol.*, 153:163-168 (1983)); the transformants were grown to saturation and spotted on Leu-/Trp- plates containing increasing concentrations of copper (from 0.1-2.5 mM) and grown for 5 days at 30° C.

Figure 2A:
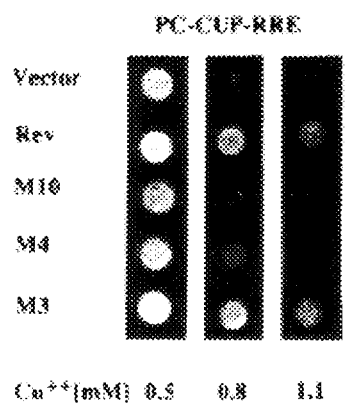
FIG. 2A–2F is a photograph of culture plates showing the results of experiments on the effects of wild-type or mutant Rev on pre-mRNA export and pre-mRNA splicing as measured by growth on copper-containing plates.
Figure 2B:
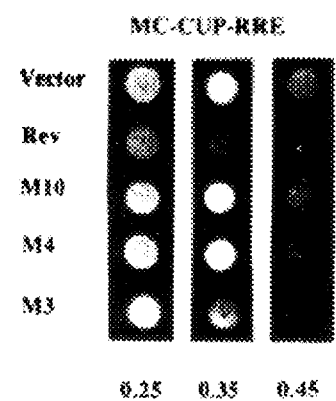
Figure 2C:
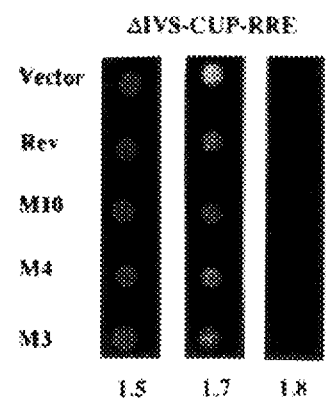
Figure 2D:
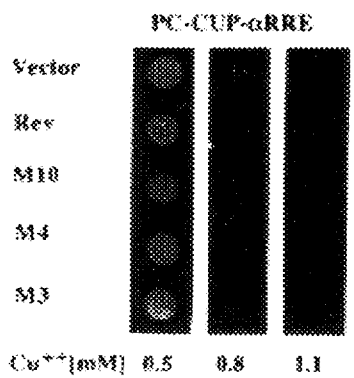
Figure 2E:
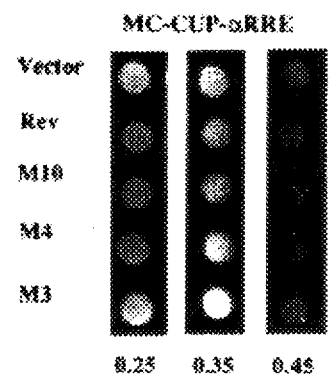
Figure 2F:
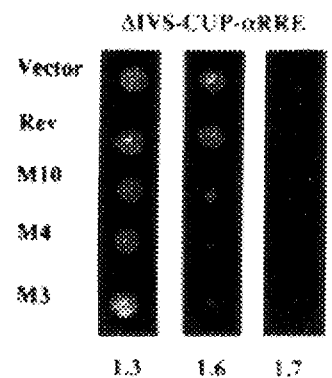

As a control for splicing- or intron-dependence, Rev-expressing strains containing the intronless ΔIVS-CUP-RRE or ΔIVS-CUP-αRRE reporter constructs were tested for growth on copper (FIG. 2C). No effect of Rev on the expression of either intronless construct was consistently observed, suggesting that the effects of Rev are restricted to or substantially enhanced with intron-containing transcripts.

Rev effects and their RRE-dependence were verified by primer extension analysis as described below, in which CUP1 pre-mRNA and mRNA levels as well as their ratios (P/M) were compared after liquid growth (Table 1).

TABLE 1

Relative CUP1 pre-mRNA and mRNA levels in strains expressing wild-type or mutant Rev.

| | Vector | Rev | M10 |
|---|---|---|---|
| | | P/M | |
| PC-CUP-RRE | $4.5\left(\frac{36}{7.8}\right)$ | $8.4\left(\frac{41}{4.9}\right)$ | $4.0\left(\frac{27}{6.5}\right)$ |
| PC-CUP-αRRE | $4.8\left(\frac{20}{4.15}\right)$ | $5.2\left(\frac{31}{5.9}\right)$ | $5.2\left(\frac{34}{6.5}\right)$ |
| MC-CUP-RRE | $2.2\left(\frac{29}{12.8}\right)$ | $4\left(\frac{36.5}{9}\right)$ | $2.2\left(\frac{33.5}{15}\right)$ |
| MC-CUP-αRRE | $1.48\left(\frac{28.5}{19}\right)$ | $1.45\left(\frac{23}{16}\right)$ | $1.52\left(\frac{30.5}{20}\right)$ |
| | | M | |
| ΔIVS-CUP-RRE | 100 | 130 | 130 |
| ΔIVS-CUP-αRRE | 96 | 92 | 105 |

RNA extractions and primer extensions were carried out according to published procedures (Pikielny, C. W. and Rosbash, M., "mRNA splicing efficiency in yeast and the contribution of nonconserved sequences," *Cell*, 41:119-126 (1985)) using two oligonucleotide primers. Oligo DT2965 is complementary to positions 29 to 51 downstream of the ATG of the CUP1 gene (Karin, M., et al., "Primary structure and transcription of an amplified genetic locus: the CUP1 locus of yeast," *Proc. Natl. Acad. Sci. USA*, 81:337-341 (1984)). Oligo DT163 is complementary to positions 26 to 43 of yeast U1 snRNA and was used as an internal control for loading. Extension products were analyzed on 6% polyacrylamide denaturing gels. The extended products were quantified by using a PhosphoImager (Molecular Dynamics, Sunnyvale, Calif.).

Total RNA was extracted from strains (FIGS. 2A-2F) containing the PC-CUP-RRE (lanes 1-3), PC-CUP-αRRE (Lanes 4-6), MC-CUP-RRE (lanes 7-9), MC-CUP-αRRE (lanes 10-12), ΔIVS-CUP-RRE (lanes 13-15) or ΔIVS-CUP-αRRE (lanes 16-18) in the presence of plasmids expressing no protein (vector) (lanes 1, 4, 7, 10, 13 and 16), wild-type Rev (lanes 2, 5, 8, 11, 14, and 17) or the effector domain mutant Rev, M10 (lanes 3, 6, 9, 12, 15 and 18). The PaNAs were reverse transcribed (Pikielny, C. W. and Rosbash, M., "mRNA splicing efficiency in yeast and the contribution of nonconserved sequences," *Cell*, 41:119-126 (1985)) with a primer complementary to the CUP1 RNA sequence. A primer specific for U1 snRNA was added to the reactions as an internal control. The primer extended bands corresponding to CUP1 pre-mRNA and mRNA and to U1 snRNA are indicated.

Example 3: Effects of Rev Expression on Pre-mRNA Export or Pre-mRNA Splicing

To examine the effects of Rev on pre-mRNA export, yeast strains containing one of the CUP1 reporter constructs were transformed with Rev expressing plasmids or a "vector" control plasmid containing no Rev coding sequence. Wild-type as well as three mutant Rev coding sequences (M10, M4, and M3) (Malim, M. H., et al., "Functional dissection of the HIV-1 Rev trans-activator—derivation of a trans-dominant repressor of Rev function," *Cell*, 58:205-214 (1989)) were expressed from a low copy number TRP/CEN3 derivative of the yeast pG1 vector behind the strong constitutive GPD (glyceraldehyde-3-phosphate dehydrogenase) promoter (Bitter, G. A. and Egan, K. M., "Expression of heterologous genes in *Saccharomyces cerevisiae* from vectors utilizing the glyceraldehyde-3-phosphate dehydrogenase gene promoter," *Gene*, 32:263-274. (1984); Schena, M. and Yamamoto, K. R., "Mammalian glucocorticoid receptor derivatives enhance transcription in yeast," *Science*, 241:965-967 (1988)). M10 has a two amino acid substitution in the Rev effector domain. This mutant has lost its ability to promote pre-mRNA export in mammalian systems but still exhibits normal RRE binding/oligomerization in vitro. M4 has a three amino acid substitution in the RNA binding, Arg-rich domain of the protein. This mutant is unable to promote pre-mRNA export in vivo and fails to oligomerize and bind the RRE in vitro. M3 has a two amino acid substitution close to the amino-terminus of the protein. As it has no detectable effect on Rev function in higher eukaryotics, it was used as a pseudo-wild-type control (Malim, M. H., et al., "Functional dissection of the HIV-1 Rev trans-activator—derivation of a trans-dominant repressor of Rev function," Cell, 58:205-214 (1989); Zapp, M. L., et al., "Oligomerization and RNA binding domains of the type 1 human immunodeficiency virus Rev protein: a dual function for an arginine-rich binding motif," Proc. Natl. Acad. Sci. USA, 88:7734-7738 (1991)). The Western blot analysis using a rabbit polyclonal anti-Rev antibody showed that all four proteins (wild-type, M10, M4 and M3) accumulated to comparable levels in yeast (data not shown). Immunostaining with the same anti-Rev antibody indicated that, as in mammalian cells (Felber, B. K., et al., "Rev protein of human immunodeficiency virus type 1 affects the stability and transport of the viral mRNA," Proc. Natl. Acad. Sci. USA, 86:1495-1499 (1989); Malim, M. H., et al., "The HIV-1 rev trans-activator acts through a structured target sequence to activate nuclear export of unspliced vital mRNA," Nature, 338:254-257 (1989)), wild-type Rev as well as the M3 and M10 mutants localized to the nucleus and especially to the nucleolus. Only in the case of the M4 mutant was the nucleolar staining weaker than that observed for the wild-type protein (data not shown).

The growth of yeast double transformants containing a CUP1 reporter construct and one of the Rev expressing plasmids was analyzed at increasing copper concentrations (FIGS. 2A-2F). Yeast double transformants containing one of the CUP1 reporter constructs (FIG. 1) in the presence of no viral protein (vector), wild-type Rev or the mutant M10, M4 and M3 Rev proteins were analyzed by growth on copper-containing plates; M10 contains a mutation in the Rev effector domain; M4 contains a mutation in the Rev RNA binding/oligomerization domain; the pseudo-wild-type M3 Rev contains a mutation near the amino terminus of the protein. The strains contain the A) PC-CUP-RRE (FIG. 2A) and PC-CUP-αRRE (FIG. 2D), B) MC-CUP-RRE (FIG. 2B) and MC-CUP-αRRE (FIG. 2E), C) ΔIVS-CUP-RRE (FIG. 2C) and ΔIVS-CUP-αRRE (FIG. 2F) constructs and the indicated Rev expressing vectors. The growth of each double transformant is shown at three different copper concentrations. The results showed a clear positive Rev effect on the growth of the PC-CUP-RRE strains: those expressing wild-type Rev or the M3 pseudo-wild-type Rev grew up to 1.1-1.2 mM copper whereas the one containing the vector alone stopped growing at 0.7 mM copper (FIG. 2A). No effect was observed with either the M10 effector domain mutant or the M4 RNA binding domain mutant; these strains grew indistinguishably from the vector control. As the enhanced growth with wild-type Rev was also RRE-dependent (compare FIG. 2A (RRE) with FIG. 2D (αRRE), the data recapitulate the results obtained with mammalian cells and suggest that Rev expression enhances the transport of RRE-containing pre-mRNA from the yeast nucleus to the cytoplasm. The fact that the same mutations lead to the same effects in both systems further supports the notion that Rev activity in yeast is based on a mechanism similar to that in mammalian systems.

To address the effect of Rev on the expression of spliced mRNA, yeast strains containing the MC-CUP-RRE constructs were analyzed in an identical manner. In contrast to the enhanced expression from the pre-mRNA constructs, mRNA-derived CUP1 expression was inhibited by wild-type Rev as well as by the M3 pseudo-wild-type mutant; these strains stopped growing at 0.35-0.4 mM copper as compared to the vector control strain, which continued growing up to 0.45-0.5 mM copper (FIG. 2B). The M10 and M4 mutant Rev proteins had no detectable activity, and the inhibitory effect on mRNA expression was RRE-dependent (Compare FIG. 2B with FIG. 2E). The data suggest that the positive effect on pre-mRNA transport is accompanied by a decrease in mRNA levels. This is consistent with Rev exerting a negative effect on splicing.

Figure 3:
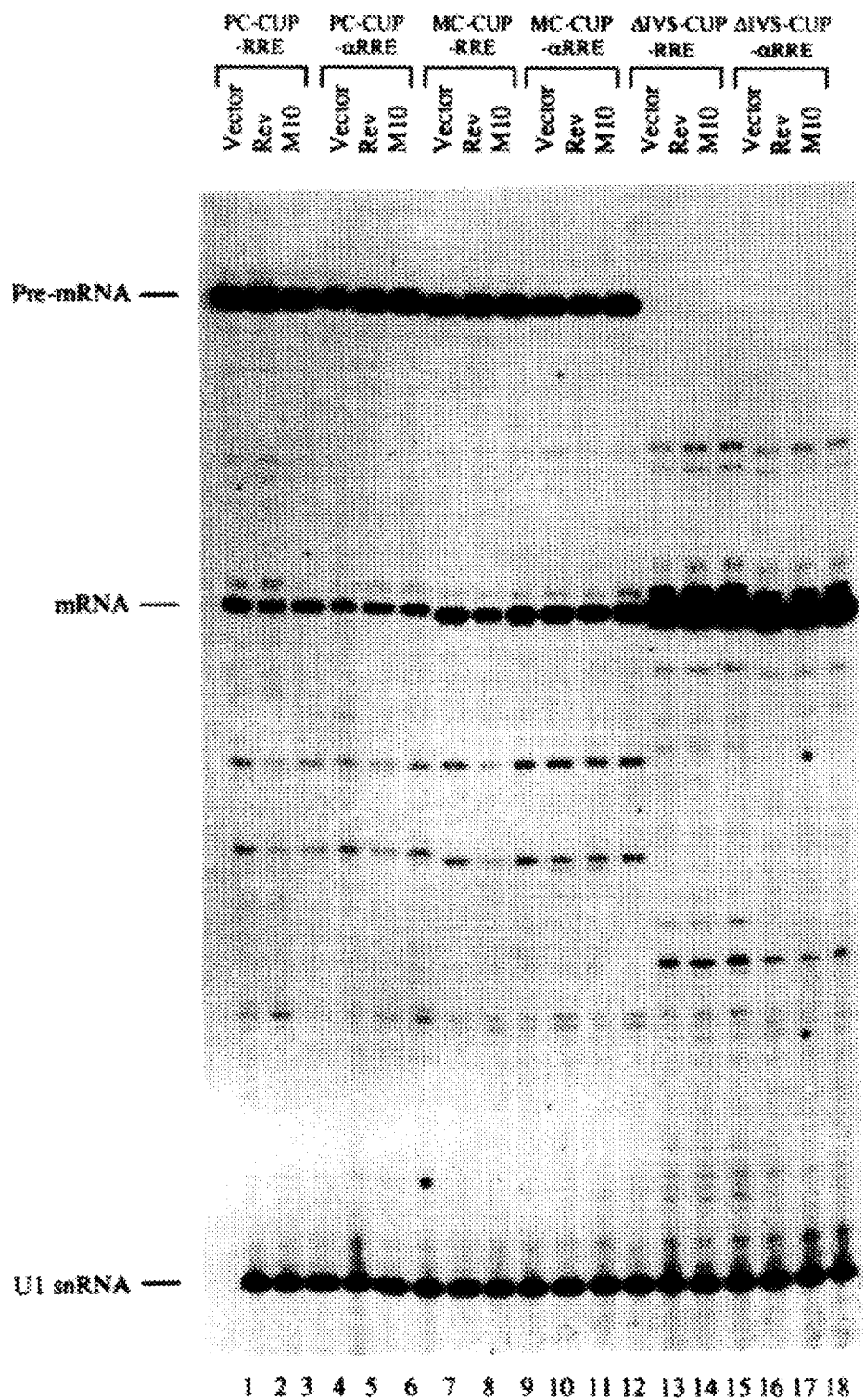
FIG. 3 is an autoradiograph showing the results of primer extension analysis of CUP1 pre-mRNA and mRNA levels in yeast double transformants expressing wild-type or mutant Rev.

In the presence of Rev, the P/M ratio of the PC-CUP-RRE or MC-CUP-RRE transcripts was increased by a factor of two, resulting from a modest but reproducible increase in pre-mRNA levels and a decrease in mRNA levels (FIG. 3, lanes 1 and 2 or 7 and 8; Table 1). In the presence of the M10 mutation, the P/M ratio was close to the control value (FIG. 3, lanes 1 and 3 or 7 and 9; Table 1). The P/M ration of αRRE-containing strains was unaffected by the presence of Rev (FIG. 3, lanes 4-6 and 10-12; Table 1).

Figure 4:
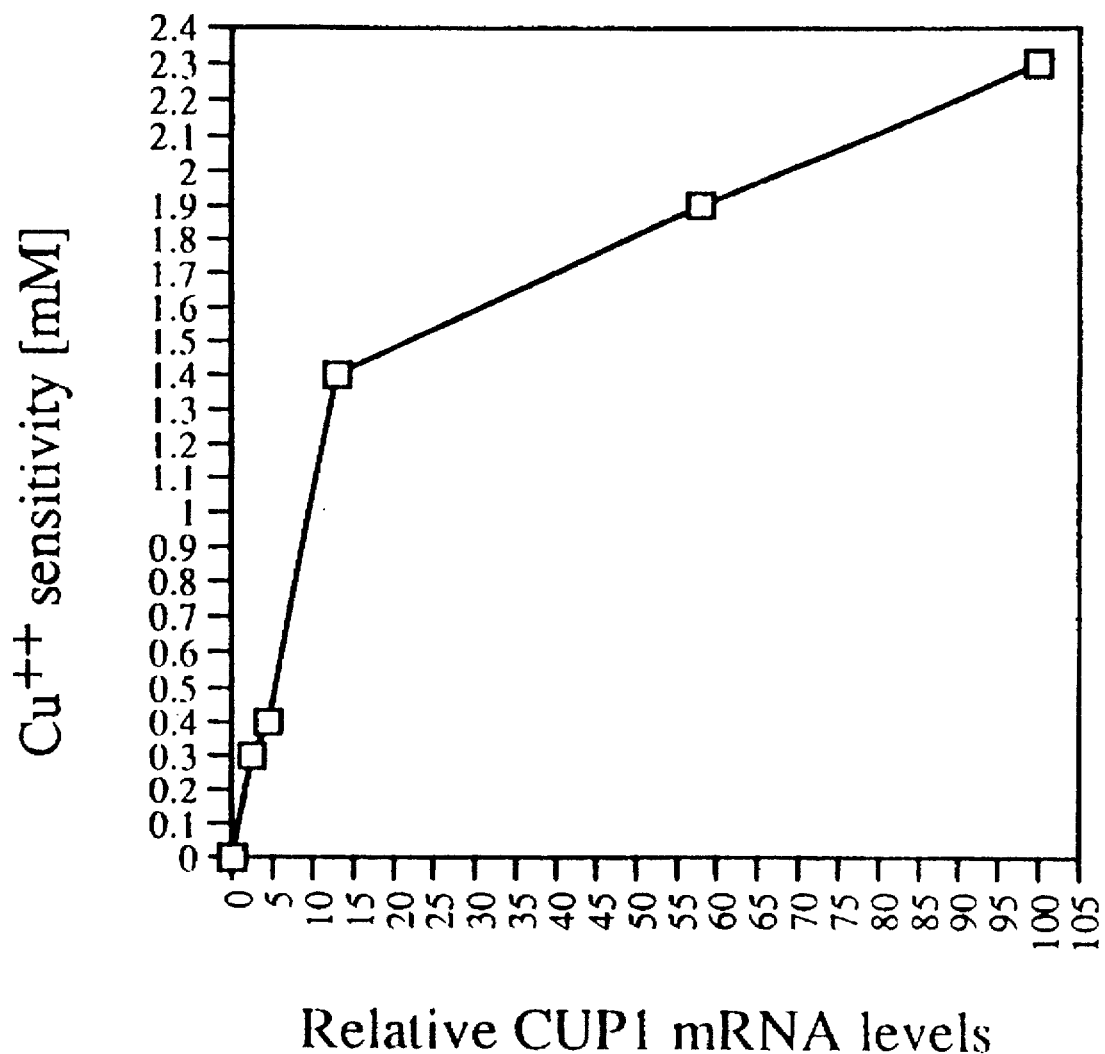
FIG. 4 is a graph showing a standard curve relating relative CUP1 mRNA levels to copper sensitivity.

Although the primer extension data and the copper resistance assay were not derived from cells grown under identical conditions (non-selective liquid growth and growth on copper plates, respectively), a quantitative estimate of the copper resistance assay indicated that the magnitudes of the effects were comparable. The sensitivity of the copper plate assay was determined by establishing a reference curve which relates relative CUP1 coding mRNA levels to copper sensitivity, i.e., the concentration of $Cu^{++}[mM]$ at which each strain dies (FIG. 4) The strains used to establish the curve contained different CUP1 reporter constructs, generating a range of CUP1 levels encoded by spliced or non intron-containing mRNAs (data not shown). The mRNA levels were determined by quantification of primer extension products using a Phosphorimager (Molecular Dynamics). The relative mRNA levels were plotted against the copper concentrations at which the corresponding yeast strains die. The growth assay is linear with respect to CUP1 mRNA levels and shows maximum sensitivity between 0.1 mM and 1.2 mM copper. The reference curve indicates that the decrease in copper resistance observed with the MC-CUP-RRE construct in the presence of Rev (from 0.5 mM to 0.35 mM copper) is due to a less than two-fold decrease in the mRNA levels, consistent with the primer extension results. In the case of the PC-CUP-RRE construct, Rev induces an increase in copper resistance (from 0.7 mM to 1.2 mM copper; FIG. 2A) that corresponds to a two-fold increase in cytoplasmic pre-mRNA levels. We interpret the absence of a corresponding change in total pre-mRNA levels (FIG. 3, lanes 1 and 2; Table 1) to the fact that Rev causes only a small fraction of the pre-mRNA to be relocalized from the nucleus to the cytoplasm.

The modest effect in yeast, compared to the 10- to 30-fold effect observed in many mammalian cell lines (Malim, M. H., et al., "Functional dissection of the HIV-1 Rev transactivator —derivation of a trans-dominant repressor of Rev function," Cell, 58:205-214 (1989); Trono, D. and Baltimore, D., "A human cell factor is essential for HIV-1 Rev action," EMBO J., 9(12):4155-4160 (1990); Huang, X., et al., "Minimal Rev-response element for type 1 human immunodeficiency virus," J. Virol., 6(4):2131-2134 (1991); Malim, M. H., et al., "Mutational definition of the human immunodeficiency virus type I Rev activation domain," J. Virol., 65:4248-4254 (1991)), may reflect only weak conservation of the relevant factors. Other interpretations of the more robust Rev effect in mammalian systems include a more complete retention of nuclear pre-mRNA in the absence of Rev or the stabilizing effect of Rev on RRE-containing pre-mRNAs (Felber, B. K., et al., "Rev protein of human immunodeficiency virus type 1 affects the stability and transport of the viral mRNA," *Proc. Natl. Acad. Sci. USA*, 86:1495–1499 (1989); Malim, M. H. and Cullen, B. R., "Rev and the fate of pre-mRNA in the nucleus: implications for the regulation of RNA processing in eukaryotes," *Mol. Cell. Biol.*, 13(10):6180–6189 (1993)).

Example 4: Effect of Splicing Signal Mutations on Pre-mRNA and mRNA Levels

To define more precisely the requirements for Rev responsiveness and to identify the possible steps in the pre-mRNA processing pathway targeted by the vital protein, mutations were introduced into the three intron key regions of the PC-CUP-RRE construct: the 5' splice site, the branchpoint, and the 3' splice site. In the 5' splice site mutant construct (PC-5'II-CUP-RRE), the highly conserved G at position +5 of the intron was replaced by an A (GUAUGU-GUAUAU) (SEQ ID NO: 3) (Parker, R. and Guthrie, C., "A point mutation in the conserved hexanucleotide at a yeast 5' splice junction uncouples recognition, cleavage and ligation," *Cell*, 41:107–118 (1985); Jacquier, A., Rodriguez, J. R., and Rosbash, M., "A quantitative analysis of the effects of 5' junction and TACTAAC box mutants and mutant combinations on yeast mRNA splicing," *Cell*, 43:423–430 (1985); Séraphin, B. and Rosbash, M., "Exon mutations uncouple 5' splice site selection from U1 snRNA pairing," *Cell*, 63:619–629 (1990)); in the branchpoint mutant (PC-3'III-CUP-RRE), the branchpoint adenosine was changed to a cytosine (UACUAAC-UACUACC) (SEQ ID NO: 4) (Jacquier, A. and Rosbash, M., "RNA splicing and intron turnover are greatly diminished by a mutant yeast branch point," *Proc. Natl. Acad. Sci. USA* 83:5835–5839 (1986)); in the 3' splice site mutant (PC-3'TC-CUP-RRE), the highly conserved AG was replaced by TC (UAG-UUC) (FIG. 5A). The 5' splice site (5' ss), branchpoint (BP) and 3' splice site (3'ss) sequences present in the wild-type (WT) PC-CUP-RRE pre-mRNA are shown at the top. The arrows correspond to the 5' and 3' cleavage sites. The CUP1 coding and the RRE sequences are indicated as boxes. The mutations in the PC-5'II-CUP-RRE (5'II), PC-3'III-CUP-REE (3'III) and PC-3'TC-CUP-RRE (3'TC) pre-mRNAs are indicated in bold below. All four introns are in frame with the CUP1 coding sequence and translation starts 8 nucleotides before the 5' splice site. Splicing to the 3' UAG splice site generates out-of-frame CUP1 mRNAs. The 3'TC mutation induces the utilization of slightly more downstream alternate 3' splice site (CAG) which gives rise to an in-frame CUP1 mRNA.

The mutant constructs were transformed into yeast, and pre-mRNA and mRNA levels were examined by primer extension (FIG. 5B). Total RNA extracted from yeast strains containing the PC-CUP-RRE (WT), PC-5'II-CUP-RRE (5'II), PC-3'III-CUP-RRE (3'III) or the PC-3'TC-CUP-RRE (3'TC constructs (lanes 1–4) was analyzed by primer extension as described in FIG. 3. Major extension products are indicated: P (in-frame CUP1 pre-mRNA), M (out-of-frame CUP1 mRNA), LI (Lariat intermediate), M2 (in-frame CUP1 mRNA resulting from splicing to the more downstream 3'AG; FIG. 5A) and U1 (U1 snRNA loading control).

The 5'II as well as the 3'III mutations strongly reduced or abolished pre-mRNA splicing, since no mRNA was detectable in these samples (FIG. 5B, lanes 2 and 3). There was also no detectable lariat-intermediate band, suggesting that both mutants cause a strong block prior to the first step of splicing. This is consistent with previous in vivo studies on these mutants in other introns and also consistent with in vitro studies that document effects of these mutations on spliceosome assembly (Rymond, B. C. and Rosbash, M., "Yeast pre-mRNA splicing," In *The Molecular and Cellular Biology of the Yeast Saccharomyces: Gene Expression*, E. W. Jones, J. R. Pringle, and J. R. Broach, eds. (Cold Spring Harbor, N.Y.: Cold Spring Harbor Laboratory Press), pp. 143–192 (1992); Moore, M. J., et al., "Splicing of precursors to mRNAs by the spliceosome," In *The RNA World*. R. F. Gesteland and J. F. Atkins, eds. (Plainview: Cold Spring Harbor Laboratory Press), pp. 303–357 (1993)). Yet pre-mRNA levels were increased in the two mutants by less than two-fold (FIG. 5B), an unusual observation for mutants with strong effects prior to the first splicing step. This is presumably due to the fact that even splicing of the wild-type version of this small synthetic intron is very inefficient (Legrain, P. and Rosbash, M., "Some cis- and trans-acting mutants for splicing target pre-mRNA to the cytoplasm," *Cell*, 57:573–583 (1989)) and wild-type pre-mRNA levels are unusually high (FIG. 5B, lane 1).

The 3'TC mutation also had no large effect on the pre-mRNA levels. There were, however, substantial levels of lariat intermediate. Also, an in-frame mRNA species was generated by the utilization of an alternate, more downstream 3'AG (FIG. 5B, lane 4; and data not shown). Consequently, the ability of PC-3'TC-CUP-RRE-containing strains to grow on copper results from mRNA as well as pre-mRNA translation. Both observations—high levels of lariat intermediate and use of a novel 3' splice site—are consistent with prior experiments indicating that the 3'AG only plays a modest role in yeast spliceosome formation and a prominent role between the first and second splicing steps (Rymond, B. C., et al., "A novel role for the 3' region of introns in pre-mRNA splicing of *Saccharomyces cerevisiae*," *Genes Dev.*, 7:238–246 (1987); Moore, M. J., et al., "Splicing of precursors to mRNAs by the spliceosome," In *The RNA World*. R. F. Gesteland and J. F. Atkins, eds. (Plainview: Cold Spring harbor Laboratory Press), pp. 303–357 (1993)).

Example 5: Effect of Splicing Signal Mutations on Rev Responsiveness

Strains containing the wild-type or mutant PC-CUP-RRE constructs were examined by growth on copper in the presence of wild-type or mutant Rev proteins (FIG. 6). Strains containing wild-type PC-CUP-RRE (panel A) or the mutant. PC-5'II-CUP-RRE (panel B), PC-3'III-CUP-RRE (panel C) and PC-3'TC-CUP-RRE (panel D) reporter constructs in the presence of wild-type or mutant M10, M4 and M3 Rev proteins were analyzed by growth on plates containing increasing copper concentrations. Like the wild-type PC-CUP-RRE strain, the PC-3'TC-CUP-RRE strain showed a higher copper resistance in the presence of Rev (FIG. 6, A and D), suggesting that the export of the mutant pre-mRNA was enhanced by the viral protein. The positive Rev effect was detectable despite the higher copper resistance induced by the 3'TC mutation (0.8 mM versus 1.2 mM; compare vector controls in FIG. 6, A and D). This higher copper tolerance is presumably due to the additional inframe mRNA generated by splicing to the alternate 3' splice site.

Figures 6A, 6B:
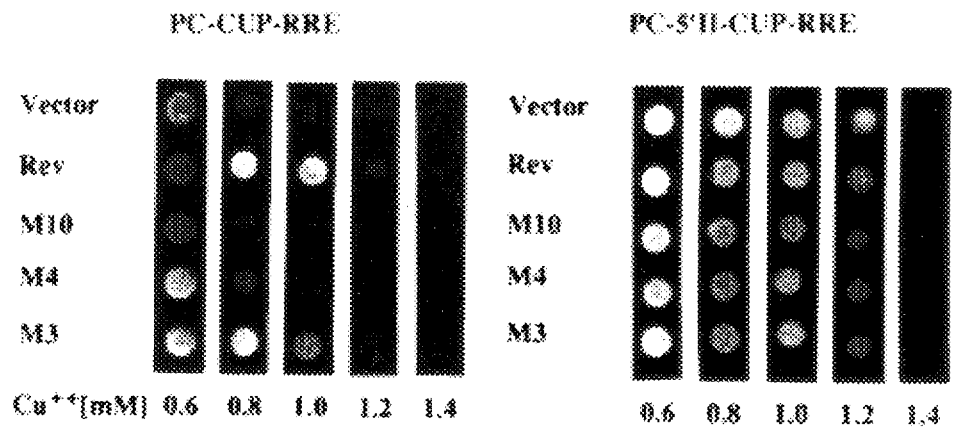
FIG. 6A–6D are photograph of culture plates showing the results of experiments determining the effect of wild-type or mutant Rev on the export of wild-type or mutant pre-mRNA.
Figures 6C, 6D:
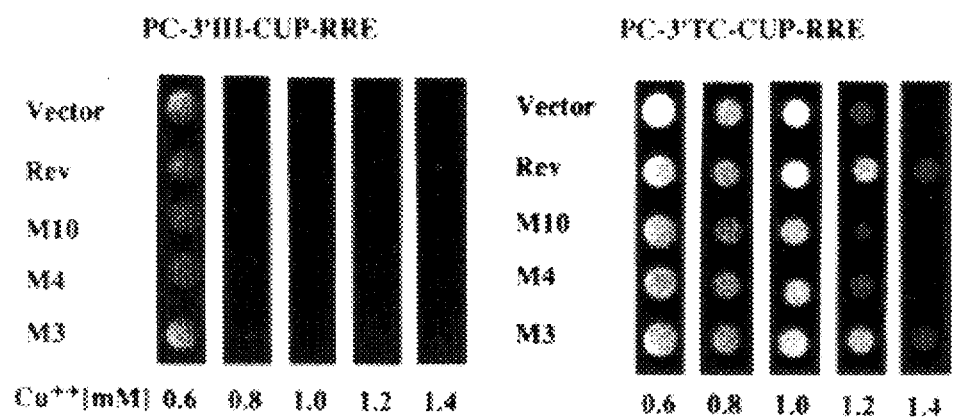

In contrast, no positive Rev effect was observed in the strain containing the PC-5'II-CUP-RRE construct. This strain also grew better than the wild-type PC-CUP-RRE control strain in the absence of Rev (0.8 mM versus 1.2 mM copper; compare FIG. 6, A and B). Although similar in magnitude to the enhanced growth of the PC-3'TC-CUP-RRE-containing strain, it is almost certainly for a different reason and likely reflects a slight (two-fold) increase in pre-mRNA escape or pre-mRNA translation. Importantly, Rev showed no additional positive effect on the export of the mutated PC-5'II-CUP-RRE pre-mRNA (FIG. 6B). The 3'III branchpoint mutation also inhibited the Rev response (FIG. 6C). However, and unlike the 5'II mutant strains, the 3'III mutant strains grew on copper identically to the wild-type strain (compare vector controls in FIG. 6, A and C). This presumably reflects the fact that the 3'III mutation has little or no effect on pre-mRNA retention.

Figure 7:
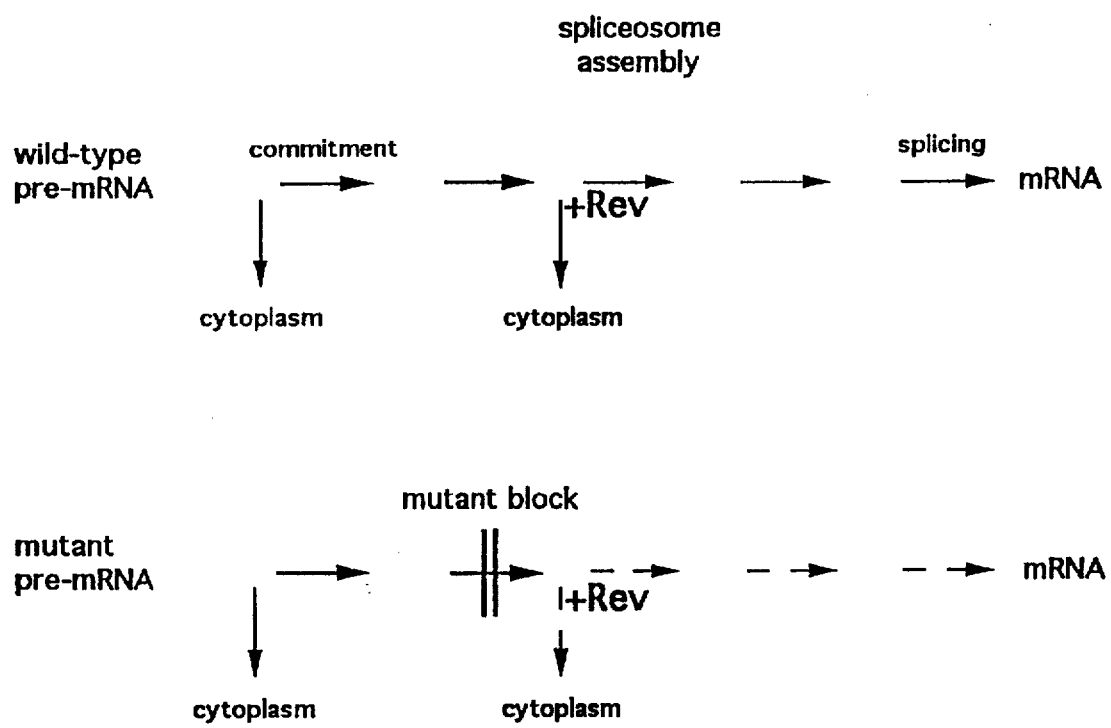
FIG. 7 is a schematic representation depicting a model based on the effects of splicing mutations.

The fact that both the 5' splice site and branchpoint mutants block the Rev response was interpreted to indicate that the viral protein undergoes a functional interaction with pre-mRNA subsequent to an early step of splicing complex formation (FIG. 7). A major fraction of the short intron-containing pre-mRNA becomes committed to the spliceosome pathway and is ultimately spliced. A small fraction of this pre-mRNA bypasses the splicing pathway and reaches the cytoplasm, as measured by pre-mRNA translation. The 5' splice site and branchpoint mutations have no major effect on pre-mRNA escape, suggesting that the mutated pre-mRNAs still undergo the early assembly or commitment steps. However the mutations inhibit splicing strongly, as represented here by a block at a specific step of spliceosome assembly. The mutations also eliminate the positive effect of Rev on pre-mRNA export, i.e., the mutations are epistatic to Rev action. This suggests that Rev acts on the pre-mRNA at or after the assembly step blocked by the mutations.

This interpretation is based on the known role of these two regions throughout yeast spliceosome formation (Rymond, B. C. and Rosbash, M., "Yeast pre-mRNA splicing," In *The Molecular and Cellular Biology of the Yeast Saccharomyces: Gene Expression*, E. W. Jones, J. R. Pringle, and J. R. Broach, eds. (Cold Spring Harbor, N.Y.: Cold Spring Harbor Laboratory Press), pp. 143–192 (1992); Moore, M. J., et al., "Splicing of precursors to mRNAs by the spliceosome," In *The RNA World*. R. F. Gesteland and J. F. Atkins, eds. (Plainview: Cold Spring Harbor Laboratory Press), pp. 303–357 (1993)); also, there is no evidence that these mutations affect pre-mRNA prior to splicing factor recognition. The failure of the 3'TC mutant to abrogate the Rev response is consistent with this scenario. Since this mutant is still splicing competent (FIG. 5B, lane 4), it provides an additional indication that Rev acts on pre-mRNA during spliceosome formation.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A method of screening a candidate agent for biological activity against HIV-1 Rev protein comprising:
   a) contacting a yeast double transformant with a candidate agent to be tested for activity against HIV-1 Rev protein, said yeast double transformant produced by introducing into a yeast strain which lacks the gene encoding a copper chelator protein:
     i) a reporter construct comprising regulatory control sequences operably linked to a DNA sequence encoding a copper chelator protein and a DNA sequence encoding the Rev Response Element, wherein the DNA sequence encoding the copper chelator protein is interrupted with a synthetic intron, and the intron sequence is out of frame with the DNA sequence encoding the copper chelator protein; and
     ii) a recombinant plasmid comprising regulatory sequences operably linked to a DNA sequence encoding the HIV-1 Rev protein,
said yeast double transformant being maintained in culture medium containing low copper concentration;
   b) increasing the copper concentration in the culture medium, and determining the growth rate of the yeast double transformant; and
   c) comparing the growth rate of the yeast double transformant grown in the presence of the candidate agent with the growth rate of the yeast double transformant grown under similar conditions but in the absence of the candidate agent to determine if the candidate agent has activity against HIV-1 Rev protein, wherein if the candidate agent has activity against HIV-1 Rev, the growth rate of the yeast double transformant cultured in the presence of the candidate agent will be greater than the growth rate of the yeast double transformant grown in the absence of the candidate agent.

2. The method of claim 1 wherein the yeast strain is *Saccharomyces cerevisiae*.

3. A method of screening a candidate agent for biological activity against HIV-1 Rev protein comprising:
   a) contacting a yeast double transformant and a yeast control strain, said yeast control strain encoding a selectable marker, with a candidate agent to be tested for activity against the HIV-1 Rev protein, said yeast double transformant produced by introducing into a defective yeast strain which lacks the gene encoding a copper chelator protein:
     i) a reporter construct comprising regulatory control sequences operably linked to a DNA sequence encoding a copper chelator protein and a DNA sequence encoding the Rev Response Element, wherein the DNA sequence encoding the copper chelator protein is interrupted with a synthetic intron, and the intron sequence is out of frame with the DNA sequence encoding the copper chelator protein; and
     ii) a recombinant plasmid comprising regulatory sequences operably linked to a DNA sequence encoding the HIV-1 Rev protein, said yeast double transformant and yeast control strain being maintained in culture medium containing low copper concentration;
   b) increasing the copper concentration in the culture medium of both strains and determining the growth rate of the yeast double transformant and the yeast control strain; and
   c) determining the ratio of the growth rate of the yeast double transformant and the yeast control strain to determine if the candidate agent has specific activity against the target molecule, wherein a candidate agent that has specific activity against the target will enhance the growth ratio of yeast double transformant to yeast control.

4. A method of claim 3 wherein the yeast strain is *Saccharomyces cerevisiae*.

5. A method of screening a library of DNA sequences encoding peptides to determine the biological activity of one or more of the peptides encoded by the DNA sequences against HIV-1 Rev protein, comprising:
   a) introducing into a yeast strain which lacks a gene encoding a copper chelator protein:
     i) a reporter construct comprising regulatory control sequences operably linked to a DNA sequence encoding a copper chelator protein and a DNA sequence encoding the Rev Response Element, wherein the DNA sequence encoding the copper chelator protein is interrupted with a synthetic intron; and
     ii) a recombinant plasmid comprising regulatory sequences operably linked to a DNA sequence encoding HIV-1 Rev protein,
the introduction of the reporter construct and the recombinant plasmid thereby producing yeast double transformants;
   b) introducing into the yeast double transformants of step a) plasmids containing DNA sequence inserts obtained from a random library of DNA sequences which are expressed in the yeast;
   c) maintaining said yeast double transformants expressing said library of DNA sequences of step b) under permissive culture conditions;

d) altering the culture conditions to restrictive growth conditions and maintaining the yeast double transformants expression said library of DNA sequences of step c) for sufficient time to kill or severely retard the growth of the yeast double transformants expressing said library of DNA sequences in which the activity of the HIV-1 REV is not inhibited;

e) harvesting the yeast double transformants expressing said library of DNA sequences which grow more rapidly under restrictive conditions; and f) determining the nucleotide sequences of said DNA sequence inserts present in the yeast double transformants.

6. A reporter gene construct which is expressed in yeast comprising:

a) a promoter sequence and transcription initiation site sufficient to direct transcription of a gene sequence in yeast;

b) a nucleotide sequence encoding CUP1, wherein a synthetic intron sequence containing a consensus 5' splice site, branchpoint and 3' splice site sequence interrupts the CUP1 coding sequence, said intron sequence being out-of-frame frame with the CUP1 coding sequence;

c) a nucleotide sequence encoding the HIV-1 Rev Response Element; and d) a transcription termination sequence, wherein said sequences are operably linked for expression of the reporter gene construct in yeast.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GUAUGUUAAU AUGGUUAACG UCGCGACCGU GUUUUUGAUA UCUAUACUAA CAGGCCUUUU    60

AAUAG                                                               65
```

( 2 ) INFORMATION FOR SEQ ID NO:2:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GUAUGUUAAU AUGGUUAACG UCGCGACCGU GUUUUUGAUA UCUAUACUAA CAGGCCUUUU    60

AAUAG                                                               65
```

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GUAUGUGUAU AU                                                                                          1 2

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

UACUAACUAC UACC                                                                                        1 4